United States Patent
Aoki

(10) Patent No.: US 6,579,531 B2
(45) Date of Patent: Jun. 17, 2003

(54) METHOD FOR TREATING HEART DISEASE AND CARDIOVASCULAR DISEASE IN DIABETIC AND NON-DIABETIC PATIENTS

(76) Inventor: Thomas T. Aoki, 1021 El Sur Way, Sacramento, CA (US) 95825

( * ) Notice: Subject to any disclaimer, the term of this patent is extended or adjusted under 35 U.S.C. 154(b) by 0 days.

(21) Appl. No.: 09/881,824

(22) Filed: Jun. 15, 2001

(65) Prior Publication Data

US 2001/0053380 A1 Dec. 20, 2001

Related U.S. Application Data

(60) Provisional application No. 60/212,135, filed on Jun. 16, 2000.

(51) Int. Cl.[7] ........................... A61K 38/28; A61K 31/70
(52) U.S. Cl. ........................... 424/422; 424/423; 514/3; 514/4
(58) Field of Search ................................ 424/422, 423; 514/3, 4

(56) References Cited

U.S. PATENT DOCUMENTS 4,826,810 A  5/1989  Aoki

OTHER PUBLICATIONS

Aoki, T. et al., "Effect of chronic intermittent intravenous insulin therapy on antihypertensive medication requirements in IDDM subjects with hypertension and nephropathy", Diabetes Care, 1995 Sep.; 18(9): 1260–5.*

Aoki, T. et al., "Chronic intermittent intravenous insulin therapy corrects orthostatic hypertension of diabetes", The American Journal of Medicine,, Dec. 1995; 99(6):683–4.*

Aoki, T. et al., "Effect of intensive insulin therapy on abnormal circadian pressure pattern in patients with type I diabetes mellitus", Online Journal of Curr Clinical Trials, Dec. 15, 1995; Doc No 199 (abstract).*

Aoki, T. et al., "Chronic intermittent intravenous insulin therapy: a new frontier in diabetes therapy", Diabetes Technology and Therapeutics 2001 Spring; 3(1): 111–23.*

Aoki Diabetes Research Institute, "CIIT Treatment Results", Mar. 31, 2001.*

Arnot Ogden Medical Center, "Hypertension and Heart disease", 1998.*

Heinemann, "Pulsatile insulin infusion and glucose–homeostasis in well–controlled type 1 diabetic patients", Journal of Internal Medicine 1989, vol. 226, pp. 325–330.

Aoki, T. et al., "long term intermittent intravenous insulin therapy and type 1 diabetes mellitus", The Lancet, vol. 342, Aug. 28, 1993, pp. 515–18.

* cited by examiner

Primary Examiner—Thurman K. Page
Assistant Examiner—Rachel M. Bennett
(74) Attorney, Agent, or Firm—Eric G. Masamori

(57) ABSTRACT

The present invention is a system and method capable of improving the dietary fuel capabilities and diabetics impaired patients and correct an overutilization of free fatty acids associated with heart disease in diabetic and non-diabetic patients. The current invention is the treating of heart disease and cardiovasular disease using insulin pulses to a patient utilizing Chronic Intermittent Intravenous Insulin Therapy to achieve an increase dietary fuel capabilities and correct overutilization of free fatty acids associated with heart disease in both diabetic and non-diabetic patients.

6 Claims, No Drawings

METHOD FOR TREATING HEART DISEASE AND CARDIOVASCULAR DISEASE IN DIABETIC AND NON-DIABETIC PATIENTS

CROSS REFERENCE TO OTHER APPLICATIONS

This application claims the benefit of U.S. Provisional Patent Application No. 60/212,135 filed Jun. 16, 2000.

FIELD OF INVENTION

This invention relates to the treatment of heart disease and cardiovascular disease in diabetic and non-diabetic patients. More specifically, the invention relates to a system and method for treating heart and cardiovascular diseases in diabetic and non-diabetic patients with Chronic Intermittent Intravenous Insulin Therapy.

BACKGROUND OF THE INVENTION

The main cause of death for patients with diabetes mellitus is cardiovascular disease in its various forms. Existing evidence indicates that diabetic patients are particularly susceptible to heart failure, primarily in association with atherosclerosis of the coronary arteries and autonomic neuropathy. Furthermore, recent data also supports the existence of a disease entity called "diabetic cardiomyopathy" which occurs in the absence of angiographic signs of coronary artery disease. There is little doubt that a metabolic component is present in various forms of cardiovascular disease in diabetic patients. Altered lipid metabolism (excessive lipolysis, increased free fatty acids (FFA) levels and enhanced FFA oxidation in the myocardium) and altered carbohydrate metabolism (impaired glucose oxidation in the myocardium through reduced rate of glucose utilization and depressed pyruvate dehydrogenase complex activity) lead to depressed myosin ATPase activity, decreased ability of the sarcoplasmic reticulum to take up calcium, and depression of other membrane enzymes such as $Na^+/K^+$-ATPase and $Ca^{2+}$-ATPase (Rodrigues et al. J Mol Cell Cardiol, 1995, 27:169–79). The cardiac dysfunction (lower stroke volume, cardiac index and ejection fraction and a higher left ventricular end diastolic pressure) frequently manifested by patients with type 1 diabetes, could be explained at least partially by the metabolic abnormalities outlined above, and is likely secondary to insulin deficiency since appropriate insulin administration can restore normal patterns of cardiac metabolism (Avogaro et al, Am J Physiol 1990, 258:E606–18). There is little dispute that an attempt should be made to lower elevated plasma triglyceride and FFA levels, thus decreasing the heart's reliance on FFA and, hence, overcoming the FFA inhibition of myocardial glucose utilization. The abnormalities in left ventricular systolic function may be partially reversible with improvement of metabolic control of diabetes. Recently, the DIGAMI (Diabetes mellitus, Insulin Glucose infusion in Acute Myocardial Infarction) study indicated that diabetic patients with acute myocardial infarction had a 28% reduced mortality at 1 year when treated with an insulin-glucose infusion followed by multidose insulin, compared to conventional therapy (controls) (DIGAMI, Malmberg K. Br Med J, 1997, 314:1512–15).

What is needed is a system and method that increases stroke volume, that improves cardiac index, that increases ejection fraction, and that lowers ventricular end diastolic pressure, thus improving cardiac function, as well as improving the quality of life of the patient. It is a further objective of this treatment to significantly reverse the cardiac dysfunction common to diabetic patients with heart disease, as well as heart disease in those who are not diabetic.

SUMMARY

Accordingly, the present invention is a system and method capable of improving the dietary fuel capabilities of diabetic and metabolically impaired patients and correct an overutilization of free fatty acids associated with heart disease in diabetic and non-diabetic patients. The current invention is the treating of heart disease and cardiovascular disease using insulin pulses to a patient utilizing Chronic Intermittent Intravenous Insulin Therapy to achieve an increase dietary fuel capabilities and correct overutilization of free fatty acids associated with heart disease in both diabetic and non-diabetic patients.

Diabetic heart disease is the most common complication of diabetes, experienced by both type I and type II diabetic patients. Experts generally agree that the primary fuel for both the normal and diabetic heart is free fatty acids, a fuel that requires more oxygen on a per calorie basis than glucose as a fuel. As a consequence, the heart of both diabetic and non-diabetic individuals is particularly vulnerable to ischemia. Recent studies using noninvasive intravascular ultrasound instrumentation reveal that many, if not most, of the vessels in a diabetic individual with 1 coronary artery (by angiography) disease are significantly atherosclerotic. In these patients, a blood clot can temporarily or permanently block blood flow to a portion of the myocardium. If the involved tissue had been primarily utilizing free fatty acids for energy generation, even a slight or temporary decrease in blood flow or oxygen supply would be catastrophic. On the other hand, if that tissue had been burning glucose rather than free fatty acids, for the generation of an equivalent amount of energy, a temporary disruption of blood or oxygen supply would not be as deleterious, since that tissue's oxygen requirements would be less. Thus, for the same amount of oxygen delivered to the myocardium, glucose utilization rather than free fatty acid utilization, would result in increased energy (ATP) generation.

One preferred embodiment of the invention is a system for heart disease and cardiovascular disease in diabetic and non-diabetic patients through an intravenous administration of a pulse of insulin comprises a means for determining a respiratory quotient of a patient, a liquid or food containing glucose, an intravenous site, and a means of delivering a pulse of insulin at a regular interval of time.

In the preferred embodiment of the treatment system, any instrument capable of measuring the respiratory quotient determines a respiratory quotient of a patient. The respiratory quotient is defined as the ratio of carbon dioxide produced to oxygen consumed by the patient. In the preferred embodiment, a liquid or food containing glucose is consumed by the patient to prevent hypoglycemia. The preferred liquid or food containing glucose is GLUCOLA, however any similar liquid or food containing glucose that will prevent hypoglycemia in the patient may be used.

The preferred means of delivering insulin is an infusion device. It is preferable that the infusion device is capable of providing pulses of insulin on a prearranged interval, so long as there is sufficient glucose in the blood to keep the patient from becoming hypoglycemic. The preferred infusion device is also capable of delivering the pulses of insulin in as short duration of time as possible, without adversely affecting the vein at the site of infusion is used. However, less accurate devices may deliver the pulses and achieve the needed infusion profile of approximately six minutes.

In the preferred embodiment, the intravenous site is a temporary or permanent IV access site located in the body, forearm or hand of the patient. The amount of insulin is tailored to achieve increased glucose utilization by the diseased myocardium. Improved physical activity, decreased angina and increased ejection fraction measure increased glucose utilization. Type 1 diabetic patients receive 20–35 milliunits of insulin per kilogram of body weight per pulse and type 2 diabetic patients receive 70–200 milliunits of insulin per kilogram of body weight per pulse. During periods of non-use, the IV site is preferably converted to a heparin or saline lock.

In one embodiment of the method of the invention, the patient is seated in a blood drawing chair and a 23 gauge needle/catheter is inserted into a hand or forearm vein to obtain vascular access. Although a 23 gauge needle catheter is preferred, any system of such access may accomplish the needed result, including indwelling catheters. After a short equilibration period, usually thirty minutes, the respiratory quotient (the ratio of carbon dioxide produced to oxygen consumed by the patient) of the patient is measured. The respiratory quotient measuring device may be any presently known model manufactured by any presently known supplier of such instruments. In the preferred embodiment, the patient is then asked to drink or eat liquid or food containing glucose usually on the order of 60 to 100 grams of glucose. In the preferred embodiment a pulse of insulin is administered intravenously on a regular interval of time, usually every six minutes, until the respiratory quotient (RQ) shows improvement, as indicated by a respiratory quotient of 0.90 or greater. In the preferred embodiment, improvement in RQ is generally achieved within one hour. In the preferred embodiment, the insulin/oral glucose phase is then followed by a rest period of usually one hour. In the preferred embodiment the entire procedure repeated until the desired effect is achieved.

The preferred method of insulin pulse delivery would be a prearranged interval, so long as there is sufficient glucose in the blood to keep the patient from becoming hypoglycemic. In order to determine the progress of the patient, it is preferable the RQ is measured every hour and blood glucose levels are checked every 30 minutes. The blood glucose level may be measured by any means which shows that the patient is not becoming hypoglycemic. In the preferred embodiment, the patient is free to move around after the initial insulin pulses have been administered. In the preferred embodiment, the intravenous site is converted to a heparin or saline lock. The patient returns to the blood drawing chair to receive their next series of insulin pulses. In the preferred embodiment, the subsequent insulin pulses must be covered by supplying glucose by mouth or other means. The total time of the preferred procedure is approximately 6–7 hours.

In the preferred embodiment, two successive days of three treatments are performed with a new patient. In the preferred embodiment, the above is then repeated once a week. For patients who need a more intensive approach, it is preferable the procedure be repeated 3 or more times, including continuously each week until the desired clinical outcome is achieved.

In the non-diabetic patient more glucose may be required than in the diabetic patient, but the other parameters would remain the same, including the need for a pulse delivery.

DETAILED DESCRIPTION OF THE INVENTION

The following description is provided to enable any person skilled in the art to use the invention and sets forth the best mode presently contemplated by the inventor of carrying out his invention. Various modifications, however, will remain readily apparent to those skilled in the art, as generic principles of the present invention have been defined herein.

Diabetic heart disease is the most common complication of diabetes in both type I and type II diabetic patients. Experts generally agree that the primary fuel for both the normal and diabetic heart is free fatty acids, a fuel that requires more oxygen on a per calorie basis than glucose. As a consequence, the heart of both diabetic and non-diabetic individuals is particularly vulnerable to ischemia. Recent studies using noninvasive intravascular ultrasound instrumentation reveal that many, if not most, of the vessels in a diabetic individual with 1 coronary artery (by angiography) disease are significantly atherosclerotic. In these patients, a blood clot can temporarily or permanently block blood flow to a portion of the myocardium. If the involved tissue had been primarily utilizing free fatty acids for energy generation, even a slight or temporary decrease in blood flow or oxygen supply would be catastrophic. On the other hand, if that tissue had been chronically burning glucose rather than free fatty acids, for the generation of an equivalent amount of energy, a temporary disruption of blood or oxygen supply would not be as deleterious, since that tissue's oxygen requirements would be less. Thus, for the same amount of oxygen delivered to the myocardium, glucose utilization rather than free fatty acid utilization, would result in increased energy (ATP) generation.

The present invention is a system and method capable of improving the dietary fuel capabilities of diabetics and metabolically impaired patients and correct an overutilization of free fatty acids associated with heart disease in diabetic and non-diabetic patients. The current invention is the treating of heart disease and cardiovasular disease using insulin pulses to a patient utilizing Chronic Intermittent Intravenous Insulin Therapy to achieve an increase dietary fuel capabilities and correct overutilization of free fatty acids associated with heart disease in both diabetic and non-diabetic patients.

The preferred embodiment of the invention is a system and method of delivering insulin pulses to a patient utilizing a Chronic Intermittent Intravenous Insulin Therapy. The preferred embodiment of the treatment system comprises a means for determining a respiratory quotient of a patient, a liquid or food containing glucose, an intravenous site, and a means of delivering a pulse of insulin at a regular interval of time.

The preferred means for determining a respiratory quotient of a patient is SENSORMEDIC METABOLIC MEASUREMENT CART, however any instrument capable of measuring the respiratory quotient may be used. The respiratory quotient is defined as the ratio of carbon dioxide produced to oxygen consumed by the patient.

The liquid or food containing glucose is consumed by the patient to prevent the patient from becoming hypoglycemic. The preferred liquid or food containing glucose is GLUCOLA, but any similar type of liquid or food containing glucose may be given to the patient.

The preferred means of insulin delivery would be an infusion device capable of providing pulses of insulin on a prearranged interval, so long as there is sufficient glucose in the blood to keep the patient from becoming hypoglycemic. It is also preferable that the infusion device is capable of delivering the pulses of insulin in as short duration of time as possible, without adversely affecting the vein at the site of infusion is used. A BIONICA MD-110 infusion device is preferably used to administer insulin pulses. However, less accurate devices may deliver the pulses and achieve the needed infusion profile of approximately six minutes.

In the preferred embodiment, the intravenous site is a temporary or permanent intravenous access site located in the body, forearm or hand of the patient, whereby insulin is provided by intravenous pulses in a highly accurate manner. A 23 gauge catheter is inserted into a hand or forearm vein and serves as a temporary IV access site, however any type of similar temporary or permanent intravenous access may be used. The amount of insulin is tailored to achieve increased glucose utilization by the diseased myocardium. Since there is no direct method of measuring glucose utilization by the heart except cardiac catheterization or NMR spectroscopy of the heart, the improvement in whole body RQ is used. Type 1 diabetic patients receive 20–35 milliunits of insulin per kilogram of body weight per pulse and type 2 diabetic patients receive 70–200 milliunits of insulin per kilogram of body weight per pulse. During periods of non-use, the intravenous site is preferably converted to a heparin or saline lock.

The preferred embodiment of the method of delivering insulin pulses to a patient utilizing Chronic Intermittent Intravenous Insulin Therapy is as follows. On the morning of the procedure, the patient is preferably seated in a blood drawing chair and a 23 gauge needle or catheter is preferably inserted into a body, hand or forearm vein to obtain vascular access. However, any system of such access may accomplish the needed result, including indwelling catheters, PICC lines and PORTACATHs. After a short equilibration period the patient is asked to breathe into an instrument which measures the patient's respiratory quotient. Equilibrium is achieved when consecutive measurements of the respiratory quotient, at least 5 minutes apart, are the same. In practice the equilibration period was thirty minutes, however any period of time that allows patient to establish a steady baseline, may be used. It is preferable that a SENSOR-MEDIC METABOLIC MEASUREMENT CART be used to measure the respiratory quotient, however, any presently known model manufactured by any presently known supplier of instruments capable of measuring a respiratory quotient may be used.

After the RQ is obtained, the patient is asked to consume a liquid or food containing glucose. The amount of glucose given to the patient ranged from 60 to 100 grams, however the amount of initial glucose given to the patient may vary. A pulse of insulin is then administered intravenously on a regular interval of time until the measured RQ shows improvement, as indicated by a RQ of 0.90 or greater. The usual interval of time was every six minutes, however, other regular intervals of time may be used. Improvement in RQ is generally achieved within one hour, however, the time required for RQ improvement may be shorter or longer than one hour.

The insulin/glucose phase is followed by a rest period of usually one hour. The rest period allows the elevated insulin level to return to baseline. The entire procedure is repeated until the desired effect, RQ greater than 0.90, is achieved. The preferred method of insulin delivery would be providing pulses of insulin on a prearranged interval, so long as there is sufficient glucose in the blood to keep the patient from becoming hypoglycemic. In order to determine the progress of the patient, the RQ is measured every hour and blood glucose levels are checked every thirty minutes by any means which shows that the patient is not becoming hypoglycemic.

Once the insulin pulses have been administered and the patient shows RQ improvement as indicated by a RQ of 0.90 or greater, the patient is provided a rest period. During the rest period the patient is allowed to move around until the next series of insulin pulses are administered. During the rest period the IV site is preferably converted to a heparin or saline lock. The total time of the procedure is approximately 6–7 hours.

The amount of insulin is tailored to achieve increased glucose utilization by the diseased myocardium. Increased cardiac glucose utilization is measured by the net health outcomes of increased physical activity, decreased angina or improved ejection fraction. Type 1 diabetic patients receive 20–35 milliunits of insulin per kilogram of body weight per pulse and type 2 diabetic patients receive 70–200 milliunits of insulin per kilogram of body weight per pulse.

Usually with a new patient two successive days of three treatments are performed the first week. For continuing patients the procedure is performed once a week. For patients who need/require a more intensive approach, the procedure may be repeated 3 or more times, including continuously, each week until the desired clinical outcome is achieved. The desired clinical outcome is improved physical activity, decreased angina or improved ejection fraction. The intensive approach is designed for patients who are slow in achieving the aforementioned desired clinical outcomes.

In the non-diabetic patient more glucose may be required than in the diabetic patient, but the other parameters would remain the same, including the need for pulse delivery.

The preferred embodiments described herein are illustrative only, and although the examples given include many specificity's, they are intended as illustrative of only a few possible embodiments of the invention. Other embodiments and modifications will, no doubt, occur to those skilled in the art. The examples given should only be interpreted as illustrations of some of the preferred embodiments of the invention, and the full scope of the invention should be determined by the appended claims and their legal equivalents.

What is claimed is:

1. A method for treating heart disease and cardiovascular disease in diabetic and non-diabetic patients by improving the dietary fuel capabilities and correct an overutilization of free fatty acids comprising the steps of:
   a) determining a steady baseline respiratory quotient of a patient and obtaining a subsequent respiratory quotient every 30 minutes, the steady baseline respiratory quotient being two identical consecutive respiratory quotients less than 0.90 measured five minutes apart,
   b) having the patient consume a liquid or food containing 60 to 100 grams of glucose,
   c) administering a pulse of insulin through an intravenous site at a six minute interval of time until the subsequent respiratory quotient shows an improvement over the steady baseline respiratory quotient, the pulse of insulin being 20 to 35 milliunits of insulin per kilogram of body weight for a non-diabetic and a Type I diabetic, the pulse of insulin being 70–200 milliunits of insulin per kilogram of body weight for a Type II diabetic, the improvement over the steady baseline respiratory quotient being a respiratory quotient of 0.90 or greater, the subsequent respiratory quotient improvement over the steady baseline respiratory quotient being a measurement of increased glucose utilization by a diseased myocardium;
   d) allowing the patient to rest one hour, and
   e) repeating the steps a–d at least three times.

2. The method of claim 1, wherein the intravenous site further comprises a needle or catheter located in the patient's body, hand or forearm.

3. The method of claim 1, wherein the pulse of insulin is administered by an intravenous infusion device.

4. The method of claim 1, wherein the intravenous site is converted to a heparin or a saline lock during step (d).

5. The method of claim 1, wherein said steps a–e are repeated at least once a week.

6. The method of claim 5, wherein said steps a–e are repeated three or more times a week.

* * * * *